US010172972B2

(12) United States Patent
Desmaison et al.

(10) Patent No.: US 10,172,972 B2
(45) Date of Patent: Jan. 8, 2019

(54) DRESSING HAVING SUSTAINED RELEASE OF ACTIVE AGENTS

(71) Applicant: LABORATOIRES URGO, Chenove (FR)

(72) Inventors: Nadège Desmaison, Tart le Haut (FR); Aurélie Ruault, Dijon (FR); Stéphane Auguste, Ruffey les Echirez (FR)

(73) Assignee: Laboratoires Urgo, Chenove (FR)

( * ) Notice: Subject to any disclaimer, the term of this patent is extended or adjusted under 35 U.S.C. 154(b) by 56 days.

(21) Appl. No.: 14/414,562

(22) PCT Filed: Jul. 11, 2013

(86) PCT No.: PCT/EP2013/064718
§ 371 (c)(1),
(2) Date: Jan. 13, 2015

(87) PCT Pub. No.: WO2014/009488
PCT Pub. Date: Jan. 16, 2014

(65) Prior Publication Data
US 2015/0165086 A1  Jun. 18, 2015

(30) Foreign Application Priority Data
Jul. 13, 2012  (FR) ...................... 12 56829

(51) Int. Cl.
*A61L 15/28* (2006.01)
*A61L 15/44* (2006.01)
*A61K 8/02* (2006.01)
*A61K 8/60* (2006.01)
*A61L 15/20* (2006.01)
*A61L 15/42* (2006.01)
*A61L 15/58* (2006.01)
*A61Q 19/06* (2006.01)

(52) U.S. Cl.
CPC ............ *A61L 15/44* (2013.01); *A61K 8/0204* (2013.01); *A61K 8/0208* (2013.01); *A61K 8/60* (2013.01); *A61L 15/20* (2013.01); *A61L 15/28* (2013.01); *A61L 15/425* (2013.01); *A61L 15/58* (2013.01); *A61Q 19/06* (2013.01); *A61K 2800/56* (2013.01); *A61L 2300/232* (2013.01); *A61L 2300/412* (2013.01); *A61L 2300/602* (2013.01); *A61L 2420/02* (2013.01)

(58) Field of Classification Search
CPC ..................................................... A61L 26/00
See application file for complete search history.

(56) References Cited

U.S. PATENT DOCUMENTS

| | | | |
|---|---|---|---|
| 4,102,340 A | 7/1978 | Mesek et al. | |
| 4,901,714 A | 2/1990 | Jensen | |
| 5,702,669 A * | 12/1997 | Green | A61L 2/206 422/287 |
| 5,961,478 A | 10/1999 | Timmermans | |
| 6,096,942 A | 8/2000 | Hack | |
| 6,270,792 B1 | 8/2001 | Guillemet et al. | |
| 6,954,907 B2 | 10/2005 | Nakano et al. | |
| 2002/0046042 A1 | 4/2002 | Tamura et al. | |
| 2007/0224230 A1 | 9/2007 | Fabre et al. | |
| 2008/0312574 A1 | 12/2008 | Pernot | |
| 2010/0056971 A1 | 3/2010 | Quinon | |
| 2010/0159192 A1 * | 6/2010 | Cotton | A61L 15/42 428/137 |
| 2010/0204174 A1 * | 8/2010 | Laurensou | A61K 8/8158 514/53 |
| 2010/0285129 A1 * | 11/2010 | Laurensou | A61K 31/505 424/484 |
| 2011/0052739 A1 * | 3/2011 | Rival | A61K 8/64 424/757 |
| 2011/0126972 A1 | 6/2011 | Frerot | |
| 2012/0245120 A1 | 9/2012 | Fabre et al. | |
| 2013/0018336 A1 | 1/2013 | Pernot | |
| 2013/0034596 A1 | 2/2013 | Apert et al. | |
| 2013/0102947 A1 | 4/2013 | Auguste | |
| 2014/0058310 A1 | 2/2014 | Pernot et al. | |
| 2014/0114268 A1 | 4/2014 | Auguste et al. | |
| 2014/0142526 A1 | 5/2014 | Auguste et al. | |
| 2014/0154188 A1 | 6/2014 | Derain | |
| 2014/0364788 A1 | 12/2014 | Lecomte et al. | |

FOREIGN PATENT DOCUMENTS

| | | |
|---|---|---|
| CA | 1292185 C | 11/1991 |
| EP | 1435247 A1 | 7/2004 |
| FR | 2759379 | 1/2010 |

(Continued)

OTHER PUBLICATIONS

Edlund, U., et al.: Abstract: "Sterilization, Storage Stability and in vivo Biocompatibility of Poly(Trimethylene Carbonate)/Poly(Adipic Anhydride) Blends," Biomaterials, vol. 21, Issue 9, May 2000, pp. 945-955.

Silindir, M. et al., "The Effect of Radiation on a Variety of Pharmaceuticals and Materials Containing Polymers", PDA J Pharm Sci and Tech, vol. 66, 2012, pp. 184-199 (19 pages).

(Continued)

*Primary Examiner* — Brian Gulledge
(74) *Attorney, Agent, or Firm* — Harness, Dickey & Pierce, PLC

(57) ABSTRACT

The present disclosure relates to novel dressings containing polysulfated oligosaccharides having sustained release of the active ingredients. It also relates to a method for the preparation thereof, this method including a treatment step with ethylene oxide. It further relates to the uses thereof for wound care and the treatment and/or prevention of scars and stretch marks.

18 Claims, 2 Drawing Sheets

(56) References Cited

FOREIGN PATENT DOCUMENTS

| | | |
|---|---|---|
| WO | WO-8905645 A1 | 6/1989 |
| WO | WO-9312275 A1 | 6/1993 |
| WO | WO-9410954 A1 | 5/1994 |
| WO | WO-9519795 A1 | 7/1995 |
| WO | WO-9530394 A1 | 11/1995 |
| WO | WO-9822114 A1 | 5/1998 |
| WO | WO-0001425 A1 | 1/2000 |
| WO | WO-03032881 A2 | 4/2003 |
| WO | WO-2006007844 A1 | 1/2006 |
| WO | WO-2007008531 A1 | 1/2007 |
| WO | WO-2007025546 A1 | 3/2007 |
| WO | WO-2013001210 A1 | 1/2013 |
| WO | WO-2014013175 A1 | 1/2014 |
| WO | WO-2014147339 A1 | 9/2014 |

OTHER PUBLICATIONS

Lambert, B. J. et al., "Radiation and Ethylene Oxide Terminal Sterilization Experiences with Drug Eluting Stent Products", AAPS PharmSciTech, vol. 12, No. 4, Dec. 2011, pp. 1116-1126 (11 pages).
Crucq, A.-S. et al., "Effect of Gamma Irradiation on Drugs", Radiation sterilization and decontamination of pharmaceuticals and pharmaceutical raw materials, CRP Report, IEAE, 2005 (11 pages).

\* cited by examiner

DRESSING HAVING SUSTAINED RELEASE OF ACTIVE AGENTS

CROSS-REFERENCE TO RELATED APPLICATIONS

This application is a National Phase Entry of International Application No. PCT/EP2013/064718, filed on Jul. 11, 2013, which claims priority to French Patent Application Serial No. 1256829, filed on Jul. 13, 2012, both of which are incorporated by reference herein.

BACKGROUND

The present invention relates to novel dressings containing polysulfated oligosaccharides having sustained release of the said active ingredients. It also relates to a method for the preparation thereof, this method comprising a treatment step with ethylene oxide. It further relates to the uses thereof for wound care and the treatment and/or prevention of scars and stretch marks.

Oligosaccharides are carbohydrates the hydrolysis of which solely affords oses. These are sugars formed by the joining of at least two molecules of simple sugars (or oses). Oligosaccharides include sucrose also called saccharose, a double sugar formed by the condensing of 2 oses: one molecule of glucose and one molecule of fructose.

Various sulfated oligosaccharide compounds are known in the literature and have multiple biological, cosmetic and/or therapeutic activities. These compounds particularly include different salts of sucrose octasulfate such as the potassium salt of sucrose octasulfate, the sodium salt of sucrose octasulfate, the hydroxyaluminium complex of sucrose octasulfate or the amino acid salts of sucrose octasulfate. These latter compounds are known for their beneficial action in particular on problems of gastric inflammation but also on the healing.

The healing of a wound is a natural biological phenomenon, human and animal tissues being capable of repairing localised lesions via repair and regeneration processes particular thereto. The natural healing of a wound chiefly occurs in 3 successive phases each having its own cellular and molecular activity. These are successively:

The inflammatory phase which begins consecutively to trauma by the implementation of inflammatory and vascular phenomena in operation such as the forming of a blood clot composed inter alia of fibrin mediated by different cellular and molecular factors and forming a provisional matrix called "fibrinous" tissue or "yellow" tissue.

The granulation phase which is characterized by the onset at the wound site of fibroblasts and new endothelial cells needed for neovascularisation of the injured tissue. Once activated, the fibroblasts are transformed to myofibroblasts and thereby take part in the maturation of the granulation tissue.

The epithelialisation phase which is characterized by the reorganisation of the extra-cellular matrix. For example, the type-3 collagen is replaced by type-1 collagen. The proliferation of most cells is observed. These ones exhibit invasive behaviour in a first time of myofibroblast, fibroblast and endothelial cell type, and then show a substantial decrease in their activity. This phase over the longer term leads to a remodelled scar that is softened and no longer painful when the wound healing process follows a normal course. However, at this step pathological scars may occur due to poor realization of terminal healing steps.

Several general issues related to the healing process or to scars have already been the subject of research, in particular by the Applicant. One of the first problems encountered was the elimination of necrotic and/or fibrinous tissue during the inflammatory phase. Indeed, if the process of natural debridement is insufficient, whereby this tissue is eliminated, this is to the detriment of the healing process. Numerous solutions have been put forward in the past such as assisted debridement of mechanical, surgical, enzymatic, autolytic or biological type. They all have the objective of ridding wounds of their constituent fibrinous and necrotic tissue.

However these different techniques have numerous disadvantages. They prove to be too painful for the patient or too inefficient. These problems were solved through the action of compounds described in application FR 2 956 322 by Laboratoires URGO. This document describes the use of a compound selected from among polysulfated oligosaccharides having 1 to 4 ose units, the salts or complexes thereof, as wound debridement agent.

Among these compounds, the potassium salt of sucrose octasulfate was previously known for the treatment of wounds during the budding phase through its action on the fibroblasts. This action is described for example in patent applications EP 230 023, WO 89/05645 or WO 98/22114. This compound was used after performing assisted debridement of the wound and hence after removing necrotic and/or fibrinous tissue. It was therefore used on a clean, debrided wound.

The beneficial action on healing of some compounds in the family of polysulfated oligosaccharides has also been described. For example, applications FR 2 824 474 and FR 2 953 522 describe compositions containing sucralfate alone or associated with salts of transition metals for their use in the healing, the regeneration or to solve skin inflammation problems.

A further problem it was sought to solve concerned pathological scars and striae distensae (stretch marks). By pathological scars is meant atrophic, retractile or hypertrophic scars.

Stretch marks occur subsequent to rapid sudden stretching of the skin. Said stretching may result from weight gain and/or hormonal change. Each stretch mark looks like a skin tear. It is in fact dermal tissue deteriorated by a transformation phenomenon of fibroblasts to myofibroblasts. Striae distensae form parallel, elongate skin striations of several centimetres long and up to 1 centimetre in width. The stretch marks may be thin and scarcely apparent but they may have small depressions imparting an irregular aspect to the skin. At a first phase, they initially vary from pale pink to purple red (immature or inflammatory stretch marks). Over time, they tend to change colour and take on a pearly white appearance (mature stretch marks). The stretch marks then become less visible, but the scar remains. Hormonal changes associated with weight gain lead to the onset of stretch marks in numerous women during pregnancy. Genetic factors also have an influence on their onset. They may also appear in parallel with some physiological or pathological conditions and may form a symptom indicative of a genetic disease. The chief triggering factors are inflammation, mechanical stress and hormonal environment. All these factors cause stretching, disorientation and disorganisation of the collagen and elastin fibres without rupture of the supporting tissue. Stretch marks can be likened to scars (since they have undergone the same formation steps as those following after trauma to the skin). Healing thereof is currently impossible but attenuation and improvement of the lesions are possible. Curative treatments are essentially local: topical treatment with derivatives of retinoic acid or fruit acids, use of peeling or laser. However, the treatments known to date are not fully satisfactory since they are not always well tolerated and their efficacy is not fully satisfactory. There is a demand for the development of a product allowing the efficient prevention and/or treatment of stretch marks, with acceptable cutaneous tolerance.

Dressings are known, in particular from application FR 2 956 322, comprising a compound selected from the group formed of polysulfated oligosaccharides having 1 to 4 oses, the salts or derivatives thereof, preferably comprised in the coating or impregnating mass of the dressing, in order to guarantee efficient bioavailability of the active ingredient at the patient's scar site. These dressings guarantee sustained bioavailability of the active ingredient to prevent or treat problems of debridement, healing, stretch marks or pathological scars. However, it was found that after an application time of a few hours, the release of active ingredient becomes insufficient. In addition, only part of the active ingredient contained in the dressing is released onto the skin to be treated. And after an application time of a few hours a new dressing has to be applied if it is desired to maintain on the skin a sufficient level of active ingredient to reach expected efficacy. Apart from the resulting cost, regular change of dressing is not always compatible with the activities of users/patients. To obtain better treatment efficacy, it has been sought to develop dressings having much higher sustained bioavailability of active ingredient. In other words, dressings have been developed having an efficient high concentration of active ingredient at the site of injury, this efficacy being sustained in time. This result is the consequence of high, sustained release of active ingredient contained in the dressing. These new dressings therefore allow faster, more efficient patient treatment.

Additionally, a method is known in the prior art for the sterilisation of dressings via treatment with ethylene oxide. However, this type of treatment has never been applied up until now to dressings containing polysulfated oligosaccharides. In addition, it is neither mentioned nor suggested in the prior art that said treatment could lengthen the release time of an active ingredient and increase the total amount of released active ingredient, much on the contrary. It is disclosed in the prior art that all sterilisation methods (e.g. radiation sterilisation, autoclave sterilisation or even sterilisation using ethylene oxide) in theory have an unfavourable impact on the release of active ingredient contained in a dressing subject of such treatment, either because the type of sterilisation degrades the active ingredient itself or because it modifies the rheological and/or structural properties of the micro-adhering elastomeric mass in which or on which the active ingredient(s) are incorporated (Radiation effects on polypropylene/polybutylene blends, Richard J. Rolando, June 1993 Tappi Journal, Vol. 76, N°6 and Influence of processing conditions on medical material degradation/failure, Michael T. K. Ling et al., Antec 200 pages 2724 to 2730).

SUMMARY

According to one preferred embodiment, the present invention concerns a dressing comprising at least one micro-adherent interface, the said micro-adherent interface comprising at least one compound selected from among polysulfated oligosaccharides comprising 1 to 4 oses, the salts and complexes thereof, the dressing having been subjected to treatment with ethylene oxide. According to one preferred embodiment, the polysulfated oligosaccharide compound is selected from among:
  the potassium salt of sucrose octasulfate;
  the silver salt of sucrose octasulfate;
  the hydroxyaluminium complex of sucrose octasulfate.

According to one preferred embodiment, the dressing comprises from 0.5 to 2 mg/cm$^2$, preferably from 0.7 to 1.9 mg/cm$^2$, advantageously from 0.9 to 1.7 mg/cm$^2$ of compound selected from among polysulfide oligosaccharides having 1 to 4 oses, the salts and complexes thereof. According to one preferred embodiment, the micro-adherent interface structure is an adhesive elastomeric composition.

According to one preferred embodiment, the micro-adherent interface comprises:
  10 to 60% by weight of at least one tackyfying resin;
  2 to 20% by weight, preferably 12 to 16% by weight of at least one hydrocolloid compound;
  10 to 65% by weight of at least one plasticizing mineral oil;
  3 to 25% by weight of at least one elastomeric polymer.
Preferably, the layer of adhesive elastomeric mass comprises:
  0.05 to 1% by weight of at least one antioxidant agent;
  10 to 60% by weight of at least one tackifying resin;
  2 to 20% by weight, preferably 12 to 16% by weight of at least one hydrocolloid compound;
  10 to 65% by weight of at least one plasticizing mineral oil;
  3 to 25% by weight of at least one elastomeric polymer;
  1 to 15% by weight of at least one stabilising agent.
According to one preferred embodiment, the dressing comprises from 1 to 15% by weight, preferably from 5 to 10% by weight relative to the total weight of the micro-adherent interface of at least one compound selected from among polysulfated oligosaccharides having 1 to 4 oses, the salts and complexes thereof.

The invention also concerns a dressing comprising a micro-adherent interface in which there is incorporated or on which there is deposited at least one compound selected from among polysulfated oligosaccharides having 1 to 4 oses, the salts and complexes thereof, having sustained release of the said compound, characterized by a dissolution higher or equal to 4% in 5 h, higher or equal to 5% in 10 h, higher or equal to 5.5% in 15 h, higher or equal to 6% in 20 h, such as measured in accordance with the sachet method, in a dissolution medium formed of 40 mL of physiological saline. According to one preferred embodiment, the dressing exhibits sustained release of the said oligosaccharide, characterized by a dissolution higher or equal to 5% in 5 h, higher or equal to 5.5% in 10 h, higher or equal to 6% in 15 h, higher or equal to 7% in 20 h, such as measured in accordance with the sachet method, in a dissolution medium formed of 40 mL of physiological saline. According to one preferred embodiment of the invention, the micro-adherent interface imparts an adhesive power to the dressing measured on a steel plate comprised between 0.5 and 100 cN/cm, preferably between 5 and 40 cN/cm. According to another embodiment, the invention concerns a dressing for use thereof in the debridement or the healing of a wound, for use in the prevention and the treatment of stretch marks and for the prevention and the treatments of scars, in particular the pathological scars.

According to a last embodiment, the invention concerns a method for manufacturing a dressing, comprising:
  (a) the depositing or incorporation, respectively on or in the micro-adherent interface of the dressing, of at least one compound selected from among polysulfated oligosaccharides having 1 to 4 oses, the salts and complexes thereof;
(b) a treatment of the dressing with ethylene oxide.

According to one preferred embodiment, step (b) of treatment with ethylene oxide comprises at least the following steps:
(i) a pre-conditioning step;
(ii) an exposure step to ethylene oxide;
(iii) a rinsing step.

According to one preferred embodiment:
at pre-conditioning step (i) the dressing or active layer is subjected to a temperature ranging from 25 to 60° C. and relative humidity ranging from 50 to 95% for a time from 5 to 15 h;
step (ii) comprises a treatment with gaseous ethylene oxide at a pressure higher or equal to 920 mBars in a chamber having relative humidity higher or equal to 50% at a temperature higher or equal to 30° C., and for a time of at least 2 hours;
step (iii) comprises at least two successive sequences of nitrogen injection followed by an expansion.

According to a final embodiment, the invention concerns a method for the prevention and/or cosmetic treatment of stretch marks or scars or skin lesions due to stretch marks, this method comprising the application of a dressing to the skin area(s) concerned. The same method being applicable to the prevention and/or cosmetic treatment of scars or skin lesions.

Figure 1:
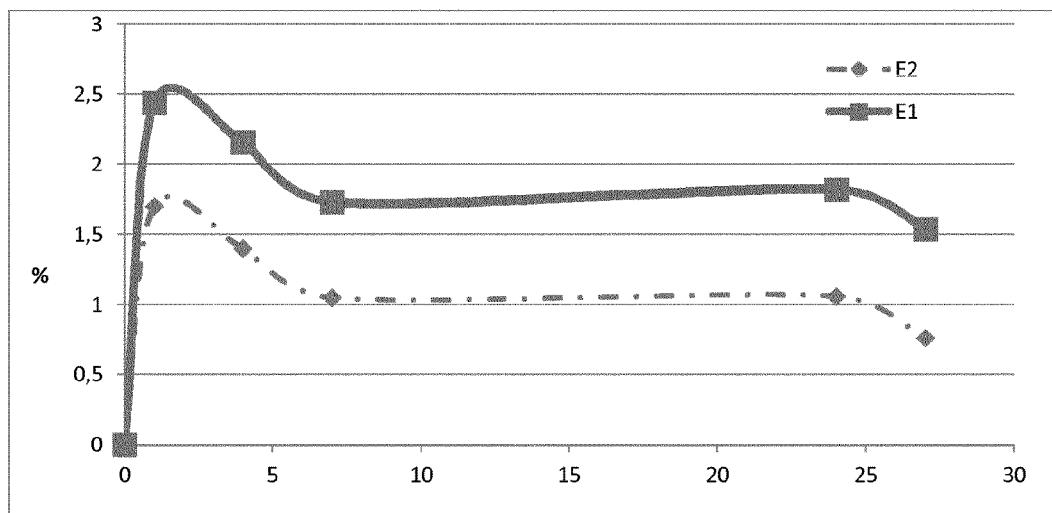
FIG. 1 is graph illustrating the non-accumulated dissolution profiles evaluated as % of active ingredient released from the dressings described in Example 1 and Example 2.

In all the Figures E1, refers to the dressing in Example No. 1 (according to the invention) and E2 to the dressing in Example No. 2 (comparative).

DETAILED DESCRIPTION

Other characteristics and advantages of the invention will become more readily apparent on reading the following description of one preferred embodiment of the invention given as an example and with reference to the appended Figures.

Most surprisingly the Applicant has developed novel dressings comprising a micro-adherent interface containing polysulfated oligosaccharides having high, sustained release of active ingredient. These dressings are obtained using a method comprising the depositing or incorporation, respectively on or in the dressing interface intended to come into contact with the skin or wound, of at least one compound selected from among polysulfated oligosaccharides having 1 to 4 ose units, this method further comprising treatment with ethylene oxide. These dressings comprise at least one compound selected from among polysulfated oligosaccharides having 1 to 4 oses, and they display sustained higher release of these active ingredients compared with dressings which have not been subjected to the treatment with ethylene oxide. The dressings of the invention comprise and are prepared from at least one compound selected from among polysulfated oligosaccharides having 1 to 4 ose units, the salts and complexes thereof.

The oligosaccharides which can be used in the present invention are oligomers formed of 1 to 4 monosaccharide units, and preferably 1 or 2 monosaccharide units, generally linked together via alpha or beta glycosidic bonding. In other words, they are mono, di, tri or tetra-saccharides, and preferably mono- or disaccharides. There is no particular limitation regarding the nature of ose units of these polysaccharides. Preferably they are pentoses or hexoses.

As examples of monosaccharides, mention can be made of glucose, galactose or mannose. As examples of disaccharides, maltose, lactose, sucrose or trehalose can be cited. As an example of trisaccharide, melezitose can be cited. As example of a tetrasaccharide, stachyose can be cited. Preferably, the oligosaccharide is a disaccharide, further preferably it is sucrose.

By "polysulfated oligosaccharide" is meant an oligosaccharide of which at least two and preferably all the hydroxyl groups of each monosaccharide have been substituted by a sulfate group. Preferably, the polysulfated oligosaccharide is sucrose octasulfate. The polysulfated oligosaccharides used in the present invention may be in the form of salts or complexes.

In general, in the present application, the expression "polysulfated oligosaccharides" includes the salts and complexes of these compounds. As examples of salts mention can be made of alkaline metal salts such as sodium, calcium or potassium salts; transition metal salts such as silver salts, zinc salts and amino acid salts. As an example of complexes, mention can be made of complexes with hydroxyaluminium.

Particularly preferred compounds for implementing the invention are the following:
the potassium salt of sucrose octasulfate,
the silver salt of sucrose octasulfate,
the hydroxyaluminium complex of sucrose octasulfate commonly known as sucralfate (for sucrose aluminium sulfate).

Preferably, the compound selected from among polysulfated oligosaccharides having 1 to 4 oses, the salts and complexes thereof is used in the manufacture of the dressing in micronized form. The above-described compounds can be used alone or in a mixture, or in combination with one (or more) other active ingredient(s) allowing induced or accelerated healing or able to play a favourable role in the treatment of a wound, or able to treat and/or prevent stretch marks or scars whether or not pathological.

Among these active ingredients, as examples, particular mention can be made of:
antibacterial agents such as silver salts or complexes (such as silver sulfates, silver nitrates, silver sulfamides or silver-containing zeolites), zinc or copper salts, metronidazole, neomycin, penicillins, clavulanic acid, tetracyclines, mynocycline, chlorotetracycline, aminoglycosides, amikacin, gentamicin, probiotics;
antiseptics such as chlorhexidine, trichlosan, biguanide, hexamidine, thymol, lugol, povidone-iodine, benzalkonium and benzethonium chloride;
pain relievers such as paracetamol, codeine, dextropropoxyphene, tramadol, morphine and the derivatives thereof, corticoids and the derivatives thereof;

local anaesthetics such as lidocaine, benzocaine, dibucaine, pramoxine hydrochloride, bupivacaine, mepivacaine, prilocaine, etidocaine;

anti-inflammatories such as non-steroidal anti-inflammatory drugs (NSAIDs), aspirin or acetylsalicylic acid, ibuprofen, ketoprofen, flurbiprofen, diclofenac, aceclofenac, ketorolac, meloxicam, piroxicam, tenoxicam, naproxen, indomethacin, naproxcinod, nimesulid, celecoxib, etoricoxib, parecoxib, rofecoxib, valdecoxib, phenylbutazone, niflumic acid, mefenamic acid.

Evidently, the compounds used in the dressings of the invention can also be used in association with one or more other compounds known for their action in the debridement phase, for example:

enzymes;
urea.

The polysulfated oligosaccharide compounds used in the dressings of the invention can also be used in association with one or more other compounds known for the treatment of stretch marks, such as:

the derivatives of retinoic acid;
fruit acids.

The polysulfated oligosaccharide compounds used in the dressings of the invention can also be used in association with one or more other compounds known for their healing action, such as: Retinol, vitamin A, vitamin E, N-acetylhydroxyproline, extracts of *centella asiatica*, papain, essential oils of thyme, niaouli, rosemary, sage, hyaluronic acid, allantoin, urea, proteolytic enzymes such as streptokinase, trypsin or collagenase, protease inhibitors.

In the present invention the polysulfated oligosaccharide compounds are integrated in a dressing via a coating or impregnation mass that is a constituent of the micro-adherent interface. By dressing in the present invention is meant any medical device of dressing type comprising at least one micro-adherent interface. In particular, the invention applies to dressings used for the treatment of wounds, and those used for the treatment of scars, cosmetic patches. The choice of dressing depends on the type of lesion to be treated. For example, absorbent dressings are preferred for the treatment of wounds since these are often highly exudative during the debridement phase.

Preferably, to promote rapid action this polysulfated oligosaccharide compound (or the coating or impregnating mass containing the same) is incorporated in the layer of dressing that comes into contact with the skin or is deposited on the surface of the dressing which comes into contact with the skin. Such depositing techniques are well known to persons skilled in the art and are described for example in patent application WO 2006/007844.

Advantageously, if the polysulfated oligosaccharide compound is not contained in a coating or impregnating mass it is deposited on the surface of the layer intended to come into contact with the skin, a layer which will have been subjected to a prior coating or impregnation step with the coating or impregnating mass devoid of polysulfated oligosaccharide compound:

either in liquid form, for example by vaporising a solution or suspension containing the same;
or in solid form, for example by sieving and/or spraying a powder containing the same.

On the other hand in the configuration in which the polysulfated oligosaccharide compound is previously included in a coating or impregnating mass, this mass is deposited on the surface of the layer intended to come into contact with the skin either continuously (via unified coating, mass or weft coating) or discontinuously (via parallel coated bands). It is also possible to formulate the polysulfated oligosaccharide compound directly in the composition of a particular layer of the dressing during the manufacture thereof.

The amount of polysulfated oligosaccharide compound used in the dressing is adapted in relation to the desired release kinetics. Advantageously, provision is made for the dressing to comprise 0.5 to 2 mg/cm$^2$, preferably 0.7 to 1.9 mg/cm$^2$, advantageously 0.9 to 1.7 mg/cm$^2$ of polysulfated oligosaccharide active ingredient. This value is related to the active surface area of the dressing i.e. the surface intended to release the active ingredient, the non-active parts of the dressing also called the "border", generally being those allowing the fixing thereof around the area to be treated.

When used in part of a dressing, the polysulfated oligosaccharide compound is incorporated in an amount such that the released amount of this compound is comprised between 70 and 140 µg/cm$^2$, preferably between 80 and 130 µg/cm$^2$ after 24 hours. This value relates to the active surface of the dressing. The dressings of the present invention comprise at least one micro-adherent interface structure such as an elastomeric layer on or in which the polysulfated oligosaccharide is deposited or incorporated.

Among the known dressings which can be used in the present invention, mentioned can be made for example of the following:

Polyurethane films, such as the products marketed by Smith&Nephew under the trade name Opsite®, or by 3M under the trade name Tegaderm® or by Laboratoires URGO under the trade name Optiskin®. These dressings are formed of a thin transparent film (in the order of 20 to 50 µm) of polyurethane with adhesive surface. Their transparency allows visual control over the area to be treated. These polyurethane films are semi-permeable; they are permeable to gas exchange and impermeable to liquids and bacteria. They impart mechanical protection against phenomena of friction, rubbing and shear.

Hydrocellular dressings, such as the products marketed by Mölnlycke under the trade name Mepilex® or by Smith & Nephew under the trade name Allevyn®, or by Laboratoires URGO under the trade name Cellosorb®. These dressings are generally formed of a backing which may be a polyurethane film or a nonwoven, of an absorbent layer which may be a polyurethane foam. The side of this absorbent layer intended to come into contact with the wound may be coated with a coating mass which may or may not be microadherent. These dressings have high absorption capability via capillarity and/or retention within the hydrocellular structure.

Hydrofibre dressings, e.g. those for example marketed by Convatec under the trade name Aquacel®. These dressings are nonwoven fibres of pure hydrocolloids (sodium carboxymethylcellulose). These dressings are highly hydrophilic and are transformed to a cohesive gel when in contact with exudate. They have very high absorption capacity and also allow the "trapping" of bacteria thereby controlling bacterial contamination.

Alginates, such as the products marketed by Smith & Nephew under the trade name Algisite® or by Coloplast under the trade name Seasorb® Soft or by Laboratoires URGO under the trade name Urgosorb®. These dressings are generally in the form of compresses or packing. They are formed of natural polysaccharides and gel when in contact with exudate. They have very high absorption capacity and are also able to "trap" bacteria thereby controlling bacterial contamination.

Hydrocolloid dressings, such as those for example marketed by Convatec under the trade name Duoderm® or by Coloplast under the trade name Comfeel® or by Laboratoires URGO under the trade name Algoplaque® or, for the general public, the product marketed by Johnson & Johnson under the trade name Compeed® or by Laboratoires URGO under the trade name URGO® Ampoules. These products are generally formed of a backing which is a polyurethane film and of an adhesive elastomeric mass containing hydrocolloids. These dressings are hydrophilic and the adhesive elastomeric mass which contains the hydrocolloids gels in contact with exudate. They adhere to healthy skin but not to the wound.

The dressings of the present invention such as those previously described comprise at least one micro-adherent interface structure e.g. an elastomeric layer on which there is deposited or in which is incorporated the polysulfated oligosaccharide. This micro-adherent interface is intended to come into contact with the skin or with the wound. To avoid causing damage to healthy tissue or to the edges of the wound, in particular when removing the dressing, preference is given to an adhesive having the property of adhering to the skin without adhering to the wound. As an example of said adhesive, mention can be made of adhesives containing silicone or polyurethane elastomers such as silicone or polyurethane gels and hydrocolloid adhesives.

Preferably, the dressings of the invention comprise a micro-adherent interface selected from among layers or composition of adhesive elastomeric mass, wherein the polysulfated oligosaccharide compound(s) are incorporated. Said adhesive elastomeric compositions are formed of an elastomeric matrix containing one or more elastomers selected from among poly(styrene-olefin-styrene) block polymers in association with one or more compounds selected from among plasticizing oils e.g. mineral oils but also associated with tackifying resins or in a preferably small amount with a hydrocolloid (from 3 to 20% by weight) such as sodium carboxymethylcellulose and, if necessary, antioxidants. The formulations of said adhesive elastomeric masses are well known and described for example in patent application FR 2 916 356.

The polysulfated oligosaccharide compound is preferably used in an amount comprised between 1 and 15% by weight, more preferably between 5 and 10% by weight relative to the total weight of the adhesive composition. Advantageously, in the dressing of the invention, the layer of adhesive elastomeric mass particularly comprises the following elements: an elastomeric compound, a hydrocolloid, at least one tackifying resin and at least one plasticizing oil. In addition, it comprises at least one compound selected from among polysulfated oligosaccharides having 1 to 4 oses, the salts and complexes thereof.

The adhesive elastomeric mass allows to formulate of a micro-adherent interface layer formed of a lipid-colloid matrix allowing to facilitate the application but also atraumatic positioning and removal of the dressing. This provisional positioning may also help carers or the user to attach the dressing using other attachment means, e.g. to cover the dressing with restraining means or adhesive tape. In this case, the interface layer can be selected so that the dressing has an adhesive power as measured by the steel plate method comprised between 0.5 and 100 cN/cm, preferably between 5 and 40 cN/cm. This adhesive power is measured as specified by standard EN 1939 wherein a dressing sample 20 mm in width and 150 mm in length is placed on a steel plate and after 10 minutes the adhesive power is measured using a dynamometer at a detachment rate of 100 mm/min and angle of 90°. By elastomeric compound is meant all poly (styrene-olefin-styrene) triblock polymers, optionally associated with diblock copolymers. The triblock copolymers may be poly(styrene-ethylene-butylene-styrene) block copolymers known as SEBS, sold under the trade name Kraton G1651®, Kraton G1654® or Kraton G1652®. The diblock copolymers may be poly(styrene-ethylene-propylene-styrene) block copolymers also known as SEPS. The elastomeric compound may also be selected from among the elastomers belonging to the family of poly(styrene-isoprene-styrene) triblock copolymers (abbreviated to poly(SIS)) and the mixtures of poly(SIS) triblock copolymers and polystyrene-isoprene) diblock copolymers.

By hydrocolloids is meant any suitable hydrocolloid compound e.g. pectin, alginates, natural plant gums (Karaya gum), cellulose derivatives such as carboxymethylcelluloses and the alkaline metal salts thereof (sodium or calcium salts of carboxymethylcellulose known under the reference CMC Blanose 7H4XF), and synthetic polymers containing salts of superabsorbent acrylic acid such as inter alia the products marketed by BASF® under the trade name Luquasorb 1003®, or by CIBA Speciality Chemicals® under the trade name Salcare SC91®, and the mixtures of these compounds. These hydrocolloids are advantageously used in particle form to prepare the adhesive composition.

The tackifying resins included in the composition of the adhesive hydrocolloid masses are selected in particular from among low molecular weight polyisobutylenes. In general, it is preferred to use hydrogenated resins such as the Escorez® series 5000 resins, and more preferably the resin Escorez 5380®.

Among the plasticizing oils which can be used to implement the invention, mention can be made of mineral oils, polybutenes or phthalate derivatives. Preferably a plasticizing mineral oil is used selected from among the products marketed by Shell® under the trade name Ondina 917®, Ondina 919® or Ondina 933®. According to one particular embodiment, a chosen amount of Ondina® oil can be substituted by an equivalent amount of Codex A® Vaseline marketed by Aiglon®.

The layer of adhesive hydrocolloid mass may comprise additional compounds such as an antioxidant, a stabilizing agent and a plasticizing compound. By "antioxidant" is meant any molecule which reduces or prevents the oxidation of other chemical ingredients. The antioxidant can be selected from among phenolic antioxidants such as the products marketed for example by CIBA-GEIGY® under the trade name Irganox 1010®, Irganox 565® and Irganox 1076® and sulfur-containing antioxidants such as zinc dibutyldithiocarbamate for example marketed by AKZO® under the trade name PERKACIT ZDBC®. Preferably the antioxidant used is Irganox 1010®. By stabilising agent is meant any compound allowing optimisation of gelling speed, wettability and even the release of active ingredients which may be contained in the composition, such as the polymer SEPINOV® EMT 10 marketed by SEPPIC, also known as the copolymer of the salt of 2-methyl-2[(1-oxo-2-propenyl) amino]-1-propanesulfonic acid and the 2-hydroxyethyl ester of propenoic acid.

Preferably, in addition to the polysulfated oligosaccharide(s), the layer of adhesive elastomeric mass essentially comprises:

10 to 60% by weight of at least one tackifying resin;
    2 to 20% by weight, preferably 12 to 16% by weight of at least one hydrocolloid compound;

10 to 65% by weight of at least one plasticizing mineral oil;
3 to 25% by weight of at least one elastomeric polymer.

Preferably, if the polysulfated oligosaccharide compound is included in the layer of adhesive elastomeric mass, this mass essentially comprises:
10 to 60% by weight of at least one tackifying resin;
2 to 20% by weight, preferably 12 to 16% by weights of at least one hydrocolloid compound;
10 to 65% by weight of at least one plasticizing mineral oil;
3 to 25% by weight of at least one elastomeric polymer;
1 to 15% by weight of polysulfated oligosaccharide.

Preferably, in addition to the polysulfated oligosaccharide(s), the layer of adhesive elastomeric mass essentially comprises:
0.05 to 1% by weight of at least one antioxidant agent;
10 to 60% by weight of at least one tackifying resin;
2 to 20% by weight, preferably 12 to 16% by weight of at least one hydrocolloid compound;
10 to 65% by weight of at least one plasticizing mineral oil;
3 to 25% by weight of at least one elastomeric polymer;
1 to 15% by weight of at least one stabilising agent.

Preferably, if the polysulfated oligosaccharide compound is included in the layer of adhesive elastomeric mass, this mass essentially comprises:
0.05 to 1% by weight of at least one antioxidant;
10 to 60% by weight of at least one tackifying resin;
2 to 20% by weight, preferably 12 to 16% by weight of at least one hydrocolloid compound;
10 to 65% by weight of at least one plasticizing mineral oil;
3 to 25% by weight of at least one elastomeric polymer;
1 to 15% by weight of at least one stabilising agent;
1 to 15% by weight of polysulfated oligosaccharide.

In the present invention the micro-adherent interface layer, also at times called micro-adherent mass, may optionally be associated with at least one of the compounds selected from among the group formed by a backing layer, an absorbent layer and non-absorbent web. Preferably, the micro-adherent interface layer is associated either with an absorbent layer alone, or with a backing layer, a non-absorbent web and an absorbent layer, or with a backing layer alone or with a backing layer and an absorbent layer. By "backing layer" is meant a layer which, in the present invention, can be formed of polymeric materials of varied nature e.g. polyamide, polyurethane, polyester, polyether, polyvinyl chloride, polyvinylidene chloride, polyvinyl alcohol, polyvinyl acetate, polystyrene, polyvinyl fluoride, a polyolefin e.g. a polyethylene or polypropylene, a material containing a polyether polyester copolymer, polyester or polyether polyurethane copolymer, a polyether polyamide copolymer.

The backing layer can be formed of a fabric in flexible, mostly scarcely extensible, non-elastic material. This backing is in the form of a fabric with large openwork mesh and can be obtained using knitting or weaving techniques allowing an openwork mesh to be obtained of regular, square or polygonal shape. In the case of weaving, the mesh can be secured by surrounding threads to obtain good dimensional stability. The mesh size is such that the unit surface area of the openings is in the order of 0.2 to 10 mm$^2$, preferably 0.5 to 10 mm$^2$ and more preferably 0.5 to 3 mm$^2$, the openwork ratio of the fabric (ratio of open surface area to total surface area) being in the order of 50 to 90%. The yarn used to manufacture the fabric is preferably a continuous strand yarn having scarcely extensible, non-elastic strands, the extensibility or rupture strength being lower than 35%. By continuous strand yarn is meant a yarn formed of one or more long twisted strands; the choice of long strands avoids the use of short fibres which may become detached from the backing and be dispersed close to the contact surface with the wound. For the same reason the constituent material of the yarn is preferably of hydrophobic type, of artificial or synthetic nature; these constituents such as polyesters, polyamides, cellulose acetates allow long strands and yarns to be obtained having many fewer fibrils than the yarns obtained from short fibres for example. The choice of some synthetic materials such as polyesters also provides the possibility of thermo-bonding the open meshwork structure of the backing. The open meshwork fabric is preferably produced using yarns of the same nature but it is also possible to use fabrics made for example with warp and weft yarns of different nature. The nature of yarn may be a polyester of polyethylterephthalate type, a polyamide or cellulose acetate for example; preferably an open meshwork fabric is used with continuous thermo-bonded yarn in polyester (Tergal or polyethylterephthalate), for example the fabrics marketed under the trade name marquisette having a gram weight of about 20 to 80 g/m$^2$ and preferably 30 to 80 g/m$^2$. These fabrics that are practically non-extensible in the warp and weft directions have the advantage of being easier to work than elastic fabrics and more regular coating of the yarn is obtained.

The backing layer may or may not be coated with adhesive on the side intended to come into contact with the skin or wound. The backing layer may be single-layer or multilayer, such as a bilayer film for example the second layer of which forms the surface opposite the surface intended to come into contact with the skin or wound. This second layer can be formed of a polymeric material of same nature as those previously mentioned or of paper which may or may not be silicone paper.

Preferably the backing layer can be formed of a continuous film and of an openwork reinforcement coated with an adhesive silicone gel of polydimethylsiloxane type, marketed under the trade name Novésil® by Zodiac®. In this case, the layer may be formed of a film or any complex integrating a film. Among the films which can be used, as an example mention can be made of films in polyurethane, polyetherurethane, polyetheramide, or polyetherester.

The reinforcement can be formed of any openwork material such as a perforated film, a thermoplastic net, a woven, a knit, or a nonwoven preferably elastic for best maintaining of the dressing on the skin. A perforated film may be in polyethylene or polypropylene for example. A woven fabric may be in polyethylene terephthalate or polyamide for example.

By absorbent layer in the present invention is meant any material or association of materials used to produce an absorbent layer in the field of dressings or hygiene products such as nappies. Among these materials, hydrophilic absorbent foams can be cited, for example polyurethane foams, textile materials in particular wovens and nonwovens containing absorbing fibres or gelling fibres, super-absorbent materials e.g. containing acrylic polymers in particular in the form of particles or fibres, preferably adhesive compositions containing hydrocolloid particles and hydrogels. As an example absorbent layer, the foams can be cited that are marketed by the companies CORPURA and RYNEL under references MCF03 and L 00562-B respectively.

One category of nonwoven is represented by the nonwovens containing cellulose fibres. These nonwovens may also incorporate particles of superabsorbent polymers commonly known as SAPs such has acrylic polymers (sodium polyacyrlates) in a proportion comprised between 10 and 60% by weight relative to the total weight of the compress to increase their absorbing capacity. Similarly, to promote the integrity of the nonwovens during absorption, the absorbing fibres can be associated with non-absorbing fibres such as thermo-binding fibres or fibres bonded together with a latex e.g. EVA latex. All these absorbing nonwovens are well known to persons skilled in the art and designated under the terms "hybrid bonded", "multibonded" or "airlaid" (see for example WO95/30394 or WO94/10954).

Accessorily, as absorbent layer, it is possible to use a combination of the previously cited nonwovens. The use of nonwovens containing gelling fibres is also well known to those skilled in the art. As examples of gelling fibres mention can be made of fibres containing hyaluronic acid, chitosan, pectin, alginates, sodium carboxymethylcellulose, sodium carboxymethylcellulose associated with alginates, chemically modified in particular carboxymethylated cellulose fibres, or fibres containing super-absorbent polymers.

As examples the fibres can be cited that are marketed under the Lanseal F trade names. As previously, these gelling fibres can be associated with other types of fibres to improve the properties of a nonwoven such has thermo-binding fibres for example. Said nonwovens and their possible different constituent fibres are described for example in the following patent applications: WO 2007/025546, WO 2007/08531, WO 93/12275, WO 00/01425, WO 94/16746, WO 95/19795, EP 878 204, EP 1 435 247 or WO 86/01400.

By super-absorbent is meant herein polymers in form of powder, fibre or any other form which gel in contact with biological liquids. Hydrophilic polymers in particle form having super-absorbent properties are described for example in application U.S. Pat. No. 4,102,340. In particular, absorbent materials such as cross-linked polyacrylamides are used for this purpose. Preferred super-absorbent particles are composed of partly neutralised cross-linked polyacrylic acid. As examples, mention can be made of the products marketed by BASF under the trade name LUQUASORB or those marketed by Ciba Speciality Chemicals under the trade name SALCARE.

In general, these super-absorbents are used in association with cellulose fibres as described in the foregoing or they are incorporated in compositions, preferably in adhesive compositions used in the hydrocolloid dressings. The absorbent layer may also be composed of these super-absorbents, either alone or incorporated between 2 distributing layers or with a nonwoven of absorbent fibres such as cellulose or viscose fibres for example (see EP 358412 or U.S. Pat. No. 6,096,942).

By non-absorbent web is meant a web inserted between the absorbent foam and the backing, intended to join them together. This joining is necessary since the surface of the backing coated with adhesive silicone gel does not adhere sufficiently to the absorbent foam, in particular in a wet environment. The web inserted between the absorbent foam and the backing is nonwoven, non-absorbent and of low gram weight. The nonwoven may be selected from among any type of nonwoven routinely used in the field of dressings and hygiene, in particular a spun laid, carded or spun lace non-woven.

It may be formed of polyamide, polyester, polyurethane and/or polyolefin fibres. According to one embodiment, the web comprises polyethylene fibres. The fibres may be single-component or bi-component of sheath/skin or side-by-side type. For example a spun laid non-woven is chosen preferably of spunbond type.

The non-absorbent web is preferably formed of hydrophobic fibres but it may also be formed of hydrophilic fibres and have been subjected to treatment to make it hydrophobic. The web may be formed of several layers provided it has sufficient porosity, the layer in contact with the adhesive silicone gel being non-absorbent and preferably hydrophobic. The web is attached to the absorbent foam over its entire surface, or preferably only on the periphery thereof using conventional bonding techniques such as heat, ultrasound, high frequency or adhesives.

According to the invention, the dressing comprising at least one compound selected from among polysulfated oligosaccharides having 1 to 4 ose units, the salts and complexes thereof, is manufactured using a method comprising at least one treatment with ethylene oxide. This ethylene oxide treatment is advantageously applied to the whole dressing.

Preferably, this process comprises at least 3 steps:
(i) a pre-conditioning step;
(ii) an exposure step to ethylene oxide;
(iii) a rinsing step.

The pre-conditioning step (i) entails subjecting the dressing to a temperature ranging from 25 to 60° C. and to relative humidity ranging from 50 to 95%. Preferably, during this step the temperature is from 30 to 55° C., advantageously from 35 to 50° C., preferably from 40 to 45° C. Preferably, at this step the relative humidity is from 55 to 90%, more preferably from 60 to 80%, further preferably from 65 to 75%. The treatment time is advantageously comprised between 5 and 15 h, preferably between 9 to 12 h. As is known per se the conditioning step can be carried out in an air-conditioned chamber e.g. an oven.

The dressings are then transferred to another chamber, subjected first to an injection of gaseous nitrogen and then to an injection of ethylene oxide, or to a simultaneous injection of both these gases, to obtain a final pressure comprised between 920 and 960 mBars; the partial pressure of ethylene oxide being comprised between 300 and 550 mBars, this pressure possibly being controlled by the mass of ethylene oxide injected into the chamber. Preferably, the relative humidity in the treatment chamber at step (ii) is higher or equal to 50%. Advantageously, the relative % [N2]/[EO] (in moles) of N2 and ethylene oxide (EO) injected into the chamber verifies:

$$0.85 \leq [N2]/[EO] \leq 2.15$$

The mass of ethylene oxide can be controlled indirectly i.e. using a mass or volume flow meter or simply by weighing.

Advantageously, step (ii) comprises a temperature rise to a level higher or equal to 30° C., preferably higher or equal to 35° C., advantageously higher or equal to 40° C. for a time of at least 2 hours, preferably at least 4 hours, advantageously at least 6 hours. This temperature rise is applied simultaneously with maintaining the dressing under ethylene oxide pressure. At the last step (iii) one or more rinsing operations are performed by injecting nitrogen into the chamber followed, by an expansion. Preferably, at least two successive rinsing operations are carried out. Preferably, the injection of nitrogen is conducted at a pressure higher or equal to 920 mBars.

According to one preferred embodiment of the invention, the dressing is a dressing comprising at least one layer containing at least one polysulfated oligosaccharide having 1 to 4 oses, treated with ethylene oxide, having sustained release of the said oligosaccharide, characterized by a dissolution higher or equal to 4% in 5 h, higher or equal to 5% in 10 h, higher or equal to 5.5% in 15 h, higher or equal to 6% in 20 h, such as measured in accordance with the sachet test method, in a dissolution medium formed of 40 mL physiological saline. Advantageously, the dressing of the invention exhibits sustained release of the said oligosaccharide, characterized by a dissolution higher or equal to 5% in 5 h, higher or equal to 5.5% in 10 h, higher or equal to 6% in 15 h, higher or equal to 7% in 20 h, such as measured in accordance with the sachet test method, in a dissolution formed of medium of 40 mL physiological saline. Advantageously the said micro-adherent interface imparts an adhesive power on a steel plate to the dressing, comprised between 0.5 and 100 cN/cm, preferably between 5 and 40 cN/cm. This adhesive power is measured using the method specified by EN 1939. The sachet test method comprises the following steps: cutting samples of the dressing and incorporating these in a permeable sachet, placing the sachets in a receptacle where they are in contact with physiological saline; collecting the liquid after a determined time; measuring the amount of active ingredient in the liquid.

The invention further concerns a dressing such as described above, for use thereof as medical device. According to one embodiment, the dressing of the invention is used to debride a wound. According to one embodiment, the dressing of the invention is used to promote wound healing. The present invention concerns a method to treat wounds comprising the use of a dressing such as described above. In this method this dressing is applied to the wound. The invention particularly concerns the debridement and healing of burns and acute or chronic wounds. It particularly concerns the debridement and/or healing of burns, radiation dermatitis, irritations of various origins, dermatitis, grazes, scratches, abrasions, cuts, leg ulcers, bedsores, wounds due to diabetes, scar-forming acne, blisters, cheilitis, eczema, nappy rash, dermatoporosis.

The activity of the compounds used in the dressings of the invention as debridement agent was evidenced in particular in the document FR 2 956 322. The activity of the compounds used in the dressings of the invention as healing and/or anti-inflammatory agent was evidenced in particular in the document FR 2 824 474.

The wound treatment method of the invention is particularly advantageous for autolytic debridement, whereby the absorbent dressing, routinely used for this technique, allows an optimal product to be obtained combining absorption of debris and degradation of fibrinous tissue. According to another embodiment, the dressing of the invention is used in the prevention or treatment of stretch marks. Compounds of polysulfated oligosaccharide type have shown significant efficacy in the prevention and treatment of stretch marks as described in the application filed under number FR 11 56431. The dressings of the invention can be used before, during or after the stretch marks formation phase, to prevent, delay and/or reduce the onset of scars or lesions on the skin due to stretch marks. These scars or lesions are not of pathological nature but have an unattractive appearance. In particular, the dressings of the invention can be used preventively in persons having a high risk of developing stretch marks (pregnancy in particular). They can also be used after the formation of stretch marks to reduce, attenuate and/or induce the disappearance of scars or skin lesions resulting therefrom. A further subject of the invention is a method for the prevention and/or cosmetic treatment of stretch marks, or scars or skin lesions due to stretch marks, this method comprising the application of a dressing on the skin area(s) concerned of a dressing. According to the invention, this application can be made before, during or after stretch marks formation.

According to another embodiment, the dressing of the invention is used to prevent and treat scars, in particular pathological scars such as acne scars, scars subsequent to surgery, cryotherapy scars, scars following after cosmetic dermatology, in particular retractile hypertrophic scars. Indeed, the compounds of polysulfated oligosaccharide type have shown significant efficacy in the prevention and treatment of scars as described in the application filed under number FR 11 56 436. The dressings of the invention can be used before, during or after the formation phase of scars to prevent, avoid, delay and/or reduce the appearance of scars on the skin. The invention particularly concerns scars or lesions having not a pathological nature but having an unsightly appearance. In particular, the dressings of the invention can be used preventively in persons having a high risk to develop scars (acne scars in particular). They can also be used after the formation of scars to reduce, decrease, attenuate and/or cause the disappearance of scars or skin lesions. A further subject of the invention is a method for the prevention and/or cosmetic treatment of scars or skin lesions, this method comprising the application of a dressing on the skin area(s) concerned of a dressing. According to the invention, this application can be made before, during or after the formation of scars or skin lesions.

The use of polysulfated compounds in dressings allowing their sustained release increases the efficacy of these active ingredients compared with the different embodiments known in the prior art. Finally, a last embodiment of the invention concerns a method of treatment with ethylene oxide of a dressing such as those described above, to increase the release of polysulfated oligosaccharides contained in the said dressing.

EXPERIMENTAL PART

1—Experimental Protocols

Protocol A: Manufacture and Composition of a Dressing Comprising a Potassium Salt of Sucrose Octasulfate in a Layer of Hydrocolloid Composition The dressing comprises a hydrocolloid micro-adherent interface layer, absorbent foam, an airlaid nonwoven, a non-absorbent polyethylene web and a backing coated with adhesive silicone gel. The following materials are used:

The backing is a 40 $g/m^2$ polyester knit coated with a silicone mass (200 $g/m^2$) laminated on a polyurethane film of 30 μm thickness and having a moisture vapour transmission rate (MVTR) higher than 10 000 $g/m^2/24$ hours. This backing has a thickness in the order of 300 μm and MVTR value in the order of 5000 $g/m^2/24$ hours.

The non-absorbent web is a 40 $g/m^2$ polyethylene nonwoven sold under the reference Vilmed® LSO 1040 WEISS by Freudenberg.

The absorbent foam is a 3 mm hydrophilic polyurethane foam sold by CORPURA under the reference MCF 03.

An absorbent nonwoven is inserted between the web and the foam; it is an airlaid nonwoven (200 $g/m^2$) containing a super-absorbent polymer marketed by EAM Corporation under the trade name Novathin®.

The peel-off protection in fluoro-silicone coated PET is 50 microns thick and formed of 2 parts or wings overlapping on the central part of the interface positioned on the patient's wound; it is supplied by SILICONATURE and marketed under the reference SILFLU® M1R88001.

The dressing is manufactured in accordance with the following method:

Preparation of the Interface Layer and Coating on the Absorbent Foam:

The following composition is prepared, expressed in weight percentage relative to the total weight.

- Mineral oil sold by Shell under the trade name Ondina® 917: 32.7%
- Carboxymethylcellulose sodium salt sold by AQUALON under the trade name CMC Blanose® 7H4XF: 14%
- Poly(styrene-ethylene-butylene) block copolymer sold by KRATON under the trade name KRATON® G 1654: 6%
- Antioxidant sold under the trade name IRGANOX® 1010 by CIBA SPECIALTY CHEMICALS: 0.1%
- Copolymer of the salt of 2-methyl-2[(1-oxo-2-propenyl) amino]-1-propanesulfonic acid and the 2-hydroxyethyl ester of propenoic acid (release agent) sold by SEPPIC under the trade name SEPINOV® EMT 10: 5%
- Tackifying resin sold by EXXON CHEMICALS under the trade name ESCOREZ® 5380: 35%.
- Potassium salt of sucrose octasulfate in micronized form: 7.5%.

The mineral oil, hydrocolloid, elastomer, KSOS then the antioxidant and release agent and finally the tackifying resin brought to a temperature comprised between 100 and 110° C. are placed in a MEL G-40 mixer to obtain a homogeneous mixture. The above mixture is discontinuously coated in an amount of 170 g/m² (±40) on the hydrophilic polyurethane foam.

Layer Assembling:

The sheet of polyethylene web is subjected to Corona treatment under the following conditions:
- Generator power: 570 watts
- Number of electrodes/width: 3/0.25 m
- Air gap setting: 2 mm
- Travel speed: 2 m/minute Before the effects of treatment with Corona have partly disappeared, a weld 2 mm in width is made on a single side of the web and hydrophilic polyurethane foam using an AMIS manual welder; the absorbent nonwoven is then inserted between the foam and web.

The last three welds are performed under the same conditions as previously to form a square 8 cm×8 cm, and the edges of the assembled complex are then cut.

The backing is cut in a square 15 cm×15 cm, and assembled onto the preceding complex by rolling using a 10 kg roller in two perpendicular directions.

The final dressing is then cut to 13 cm×13 cm, rounding the corners.

Protocol B: Method for Treating a Dressing with Ethylene Oxide

The dressings produced according to protocol A are placed in an air-conditioned chamber at a temperature oscillating between 36 and 50° C., preferably 43° C. and at a relative humidity comprised between 62 and 80%, preferably 70%, for a time of 12 h. This pre-conditioning step allows to optimize the residence time in active phase i.e. the time during which the dressings are subsequently subjected to ethylene oxide pressure. At a second step the dressings are transferred to another air-conditioned chamber. The second chamber is under an initial vacuum of 70 mbar, before any prior injection of water vapour, in order to obtain relative humidity in the order of 50%. Thereafter, a first injection of nitrogen (N2) is made under a partial pressure of 360 mbars. At the same time gaseous ethylene oxide is injected under a partial pressure of 920 mbars, and finally a second injection of nitrogen is performed bringing the partial pressure to a value of 930 mbars. The mass of ethylene oxide is then controlled and the temperature brought to 45° C. for a time of at least 6 h. At the last step, 2 successive rinsing operations are carried out by injecting nitrogen under a pressure of 970 mbars, before expanding the pressure to about 150 to 170 mbars.

Protocol C: Measurement of the Dissolution Profile of the Active Ingredient Using the Sachet Method The dissolution or release profile is measured using the so-called "sachet method". This entails performing an analysis on 3 samples of similar dressings. These samples have a surface area of 25 cm², i.e. a cut-out of 5 cm×5 cm. Each sample is previously placed in a sachet formed of a thin, permeable, hydrophobic nonwoven, and these assemblies are introduced flat in a sealed bottle, the affixed interface facing the bottom of the bottle. 40 mL of physiological saline ($H_2O$+0.9% sodium chloride) are added to each of the test bottles. Each bottle is then closed and held under tangential agitation at 120 shakes/minute at 32° C. (a temperature probe is previously placed in the thermoshake) for 1 h, 4 h, 7 h and 24 h. The entire supernatant is collected after each of these 4 time periods. After each time period, the removed liquid is replaced with 10 mL of physiological saline and each bottle is left under tangential agitation until the next set time. The amount of active ingredient contained in the supernatant is measured after each time period by HPLC chromatography (with refractometric detection).

II—Examples of Embodiment

Example No. 1: Dressing according to the invention A dressing was prepared following protocols A and B.

Example No. 2: Dressing according to the prior art A dressing was prepared following only protocol A.

Results:

The evaluation protocol C was applied to the two types of dressings. Dissolution profiles were obtained and plotted on one same graph to allow a comparison between the dressing of Example No. 1 and the dressing of Example No. 2. The dressings of Example No. 1 and Example No. 2 displayed entirely different dissolution profiles.

Figure 2:
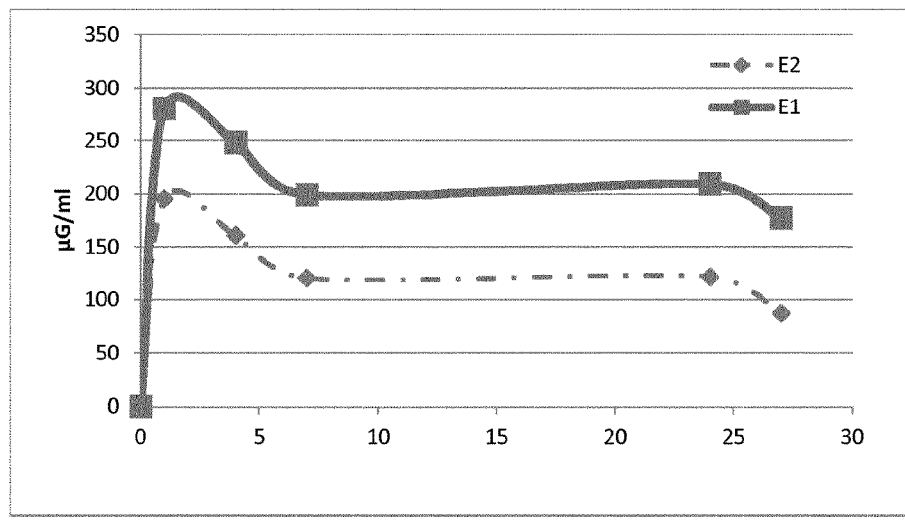
FIG. 2 is a graph illustrating the non-accumulated dissolution profiles evaluated in µg/Ml of active ingredient released from the dressings described in Example 1 and Example 2.

FIG. 1 and FIG. 2 are graphs (values of each point on the curve measured non-cumulatively with preceding values) illustrating the release of active ingredient from each dressing. The release values are defined either as a % of released active ingredient as a function of time (FIG. 1), or in µg/mL of active ingredient released as a function of time (FIG. 2). It appears very clearly that whatever the chosen graphic representation of interest, the release of active ingredient is almost twice higher for the treated dressings subject of the invention, than for the non-treated dressings. The direct consequence of this characteristic is that the efficient concentration of active ingredient found again on the lesion site is better for a dressing treated with ethylene oxide. Therefore the solving of the different problems encountered at the lesion site such as problems of healing, debridement, pathological scars or stretch marks via a higher efficient concentration of active ingredient found again at the site under consideration—that is achieved through the sustained and greater release of active ingredient—is improved.

Figure 3:
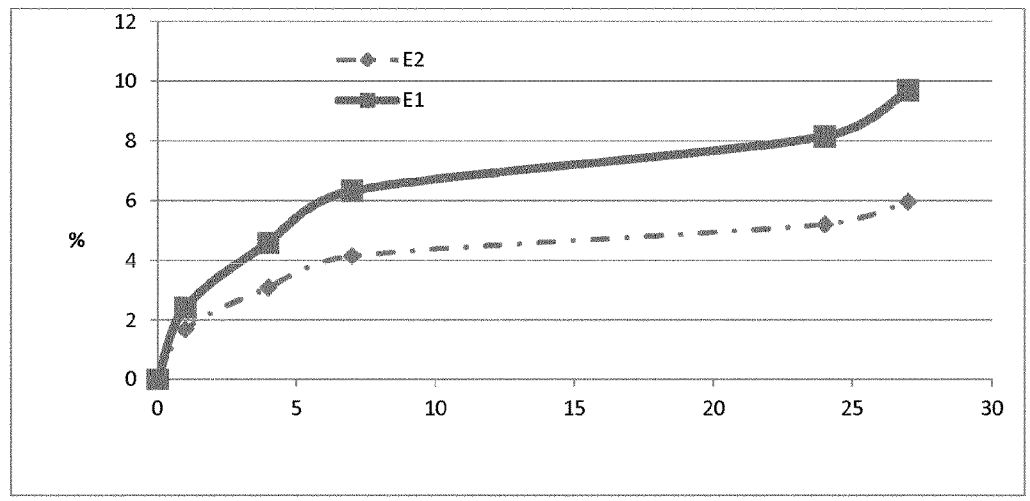
FIG. 3 is a graph illustrating the accumulated dissolution profiles evaluated as % of active ingredient released from the dressings described in Example 1 and Example 2.
Figure 4:
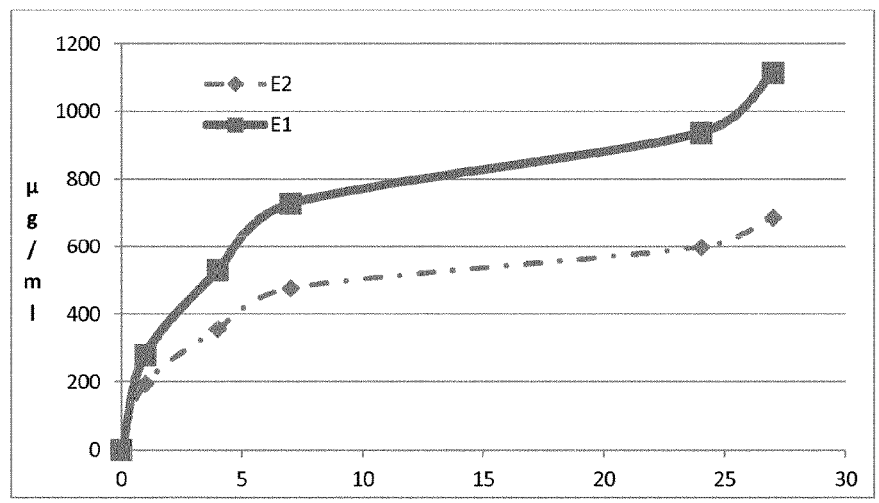
FIG. 4 is a graph illustrating the accumulated dissolution profiles evaluated in µg/Ml of active ingredient released from the dressings described in Example 1 and Example 2.

FIGS. 3 and 4 reproduce the data of FIGS. 1 and 2 respectively but the release values represent accumulated values (each value recorded at one point of the curve is added to the preceding values). This accumulation illustrates an essential characteristic of the product, the total amount released at different points in time.

Evidently the present invention is not limited to the examples and embodiments that are described and illustrated, but encompasses numerous variants accessible to persons skilled in the art.

The invention claimed is:

1. A dressing comprising at least one micro-adherent interface, in which there is incorporated or on which there is deposited 0.5 to 2 mg/cm$^2$ of at least one compound selected from among polysulfated oligosaccharides comprising 1 to 4 oses, the salts and complexes thereof, having sustained release of the compound with a dissolution higher or equal to 4% in 5 h, higher or equal to 5% in 10 h, higher or equal to 5.5% in 15 h, higher or equal to 6% in 20 h, measured in accordance with the sachet method, in a dissolution medium formed of 40 mL physiological saline, the dressing having been subjected to treatment with ethylene oxide, wherein the at least one polysulfated oligosaccharide compound is selected from among:
potassium salt of sucrose octasulfate,
silver salt of sucrose octasulfate, and
hydroxyaluminium complex of sucrose octasulfate, and wherein the dressing releases about 2 fold more of the polysulfated oligosaccharide compound as a function of time relative to a second dressing having the same micro-adherent interface, but being free from ethylene oxide treatment.

2. The dressing according to claim 1, wherein the micro-adherent interface structure is an adhesive elastomeric composition.

3. The dressing according to claim 1, wherein the micro-adherent interface comprises:
10 to 60% by weight of at least one tackifying resin;
2 to 20% by weight of at least one hydrocolloid compound;
10 to 65% by weight of at least one plasticizing mineral oil; and
3 to 25% by weight of at least one elastomeric polymer.

4. The dressing according to claim 3, wherein the hydrocolloid compound is comprised between 12 to 15% by weight.

5. The dressing according to claim 1, which comprises from 1 to 15% by weight relative to the total weight of the micro-adherent interface, of at least one compound selected from among polysulfated oligosaccharides having 1 to 4 oses, the salts and complexes thereof.

6. The dressing according to claim 5, wherein the compound selected from among the polysulfated oligosaccharides having 1 to 4 oses, the salts and complexes thereof ranges from 5 to 10% by weight, relative to the total weight of the micro-adherent interface.

7. The dressing according to claim 1, having sustained release of the polysulfated oligosaccharide, with a dissolution higher or equal to 5% in 5 h, higher or equal to 5.5% in 10 h, higher or equal to 6% in 15 h, higher or equal to 7% in 20 h, such as measured using the sachet method, in a dissolution medium formed of 40 mL physiological saline.

8. The dressing according to claim 1, wherein the micro-adherent interface imparts an adhesive power to the dressing measured on a steel plate comprised between 0.5 and 100 cN/cm.

9. The dressing according to claim 8, wherein the micro-adherent interface imparts an adhesive power to the dressing measured on a steel plate comprises between 5 and 40 cN/cm.

10. The dressing according to claim 1, wherein the micro-adherent interface comprises 0.7 to 1.9 mg/cm$^2$ of the at last one compound selected from among polysulfated oligosaccharides having 1 to 4 oses, the salts and complexes thereof.

11. The dressing according to claim 1, wherein the micro-adherent interface is adapted for application on a skin area to at least one of: treat or prevent, at least one of: stretch marks, scars due to stretch marks, or skin lesions due to stretch marks.

12. The dressing according to claim 1, wherein the micro-adherent interface is adapted for application on a skin area to at least one of: treat or prevent, at least one of: scars or skin lesions.

13. A method for manufacturing a dressing according to claim 1, the method comprising:
(a) depositing or incorporating, respectively on or in a micro-adherent interface of a dressing, at least one compound selected from among polysulfated oligosaccharides having 1 to 4 ose units, the salts and complexes thereof; and
(b) treating the dressing with ethylene oxide.

14. The method according to claim 13, wherein step (b) of treatment with ethylene oxide treatment comprises at least the following steps:
a pre-conditioning step;
(ii) an exposure step to ethylene oxide; and
(iii) a rinsing step.

15. The method according to claim 14, wherein:
at the pre-conditioning step (i) the dressing or the active layer is subjected to a temperature ranging from 25 to 60° C. and relative humidity from 50 to 95% for a time from 5 to 15 h;
step (ii) comprises treatment with gaseous ethylene oxide at a pressure higher or equal to 920 mBars in an chamber having relative humidity higher or equal to 50% at a temperature higher or equal to 30° C. for a time of at least 2 hours; and
step (iii) comprises at least two successive sequences of nitrogen injection followed by an expansion.

16. A method for the treatment of wounds, stretch marks and scars, wherein the method comprises applying a dressing according to claim 1 to the wounds, stretch marks and scars.

17. A method for the prevention and/or cosmetic treatment of a stretch mark, or a scar due to the stretch mark or a skin lesion due to the stretch mark, the method comprising applying a dressing according to claim 1 on the stretch mark, the scar due to the stretch mark or the lesion skin due to the stretch mark the area(s) of concern.

18. A method for the prevention and/or cosmetic treatment of a scar or a skin lesion, the method comprising applying a dressing according to claim 1 on the scar or the skin lesion skin area(s) of concern.

* * * * *